(12) United States Patent
Noui et al.

(10) Patent No.: US 10,624,665 B2
(45) Date of Patent: Apr. 21, 2020

(54) ULTRASONIC SURGICAL INSTRUMENT

(71) Applicants: NSK FRANCE, Paris (FR); NSK NAKANISHI INC., Tochigi (JP)

(72) Inventors: Herve Noui, Salles d'Aude (FR); Shinichi Tanaka, Tochigi (JP)

(73) Assignees: NSK FRANCE, Paris (FR); NSK NAKANISHI INC., Tochigi (JP)

( * ) Notice: Subject to any disclaimer, the term of this patent is extended or adjusted under 35 U.S.C. 154(b) by 149 days.

(21) Appl. No.: 15/123,838

(22) PCT Filed: Mar. 6, 2015

(86) PCT No.: PCT/EP2015/054771
§ 371 (c)(1),
(2) Date: Sep. 6, 2016

(87) PCT Pub. No.: WO2015/132401
PCT Pub. Date: Sep. 11, 2015

(65) Prior Publication Data
US 2017/0014152 A1    Jan. 19, 2017

(30) Foreign Application Priority Data
Mar. 7, 2014    (FR) ...................................... 14 51895

(51) Int. Cl.
*A61B 17/24* (2006.01)
*A61B 17/32* (2006.01)
(Continued)

(52) U.S. Cl.
CPC .... *A61B 17/320068* (2013.01); *A61B 17/142* (2016.11); *A61B 17/144* (2016.11);
(Continued)

(58) Field of Classification Search
CPC ........ A61B 17/320092; A61B 18/1445; A61B 17/320068; A61B 2018/0063;
(Continued)

(56) References Cited

U.S. PATENT DOCUMENTS

| | | | | |
|---|---|---|---|---|
| 5,318,570 A | * | 6/1994 | Hood | ................. A61B 17/8847 601/2 |
| 7,922,721 B2 | * | 4/2011 | Lechot | ............... A61B 17/1666 606/80 |

(Continued)

FOREIGN PATENT DOCUMENTS

| | | |
|---|---|---|
| CH | 702 066 A2 | 4/2011 |
| EP | 0 456 470 A1 | 11/1991 |

(Continued)

*Primary Examiner* — Eric J Rosen
*Assistant Examiner* — Andrew P. Restaino
(74) *Attorney, Agent, or Firm* — Faegre Drinker Biddle & Reath LLP

(57) ABSTRACT

An ultrasonic surgical instrument includes a proximal portion forming a socket attached to an ultrasonic vibration generating device and a distal portion. The instrument extends from the proximal portion to the distal portion along a main longitudinal axis and also includes a fluid channel. The distal portion includes a cutting portion, a fluid port and one or two radial bumps extending radially outwardly. The radial projections have a longitudinal position corresponding substantially to the longitudinal position of the cutting portion, whereby the radial bump provides a mark and/or a tactile location point beneath the skin for the surgeon for use in rhinoplasty or jaw surgery.

11 Claims, 7 Drawing Sheets

(51) Int. Cl.
*A61B 17/16* (2006.01)
*A61B 17/14* (2006.01)
*A61B 17/00* (2006.01)

(52) U.S. Cl.
CPC .......... *A61B 17/1659* (2013.01); *A61B 17/24* (2013.01); *A61B 2017/00738* (2013.01); *A61B 2017/00792* (2013.01); *A61B 2017/320075* (2017.08); *A61B 2217/007* (2013.01)

(58) Field of Classification Search
CPC .. A61B 2017/00477; A61B 2018/1455; A61B 2017/00734; A61B 2018/00994; A61B 2018/00607; A61B 18/1206; A61B 2017/320072; A61B 2017/00398; A61B 2018/00601; A61B 2018/00875; A61B 2017/00039; A61B 2017/00084; A61B 2018/00589; A61B 2018/00898; A61B 2018/1226; A61B 18/1447; A61B 2017/00017; A61B 2017/00424; A61B 2017/00464; A61B 2018/00767; A61B 2018/00827; A61B 2018/00988; A61B 2018/00297; A61B 2017/00026; A61B 2018/00684; A61B 2018/00904; A61B 2018/00946; A61B 2034/252; A61B 2090/061; A61B 2017/00123; A61B 2017/00199; A61B 2017/00473; A61B 2560/0209; A61B 2560/0475; A61B 2562/0219; A61B 34/76; A61B 2017/00119; A61B 2017/00225; A61B 2018/0019; A61B 18/10; A61B 2017/00876; A61B 2018/00208; A61B 2018/00636; A61B 2017/320076; A61B 2017/320084; A61B 2018/1412; A61B 2017/320074; A61B 2017/320078; A61B 17/320016; A61B 2018/00791
USPC ....... 606/169, 167, 168, 170, 171, 172, 173, 606/174, 175, 176, 177, 178, 179, 180
See application file for complete search history.

(56) References Cited

U.S. PATENT DOCUMENTS

| | | | |
|---|---|---|---|
| 9,247,952 B2 * | 2/2016 | Bleich | A61B 17/29 |
| 9,681,879 B2 * | 6/2017 | del Rio | A61B 17/1615 |
| 2008/0188878 A1 * | 8/2008 | Young | A61B 17/16 606/169 |
| 2009/0326535 A1 * | 12/2009 | Blus | A61B 17/320068 606/80 |
| 2010/0168741 A1 * | 7/2010 | Sanai | A61B 17/320068 606/42 |
| 2011/0160624 A1 * | 6/2011 | Babaev | A61B 17/320068 601/2 |
| 2013/0103066 A1 | 4/2013 | Rad | |
| 2013/0123774 A1 * | 5/2013 | Zadeh | A61B 17/16 606/39 |
| 2016/0374706 A1 * | 12/2016 | Cotter | G06F 11/2289 606/169 |

FOREIGN PATENT DOCUMENTS

| | | | | |
|---|---|---|---|---|
| EP | 0456470 | A1 * | 11/1991 | ..... A61B 17/320068 |
| EP | 0456470 | A1 * | 11/1991 | ..... A61B 17/320068 |
| EP | 2 233 085 | A1 | 9/2010 | |
| WO | 2008/012359 | A1 | 1/2008 | |
| WO | WO 2008012359 | A1 * | 1/2008 | ..... A61B 17/320068 |

* cited by examiner

ULTRASONIC SURGICAL INSTRUMENT

CROSS-REFERENCE TO RELATED APPLICATIONS

This application is the U.S. national phase of the International Patent Application No. PCT/EP2015/054771 filed Mar. 6, 2015, which claims the benefit of French Application No. 14 51895 filed Mar. 7, 2014, the entire content of which is incorporated herein by reference.

BACKGROUND

The present invention relates to surgical instruments, in particular ultrasonic instruments; on the one hand, it relates in particular to the instruments suitable for the surgical remodelling of the nasal bone structure in the field of rhinoplasty, both for reparative surgery and for plastic surgery. On the other hand it also relates to surgery operated on mandible and maxilla, both for reparative surgery and for plastic surgery.

Regarding the field of rhinoplasty, surgical operations involving the bone and/or cartilage structure of the nose can be performed following two operating techniques:
those known as 'open' techniques, wherein the structure is uncovered by lifting the skin that has previously been incised at the base of the nose,
those known as 'closed' techniques, wherein small incisions are made at the base of the nostrils in order to be able to slide a surgical instrument between the skin and the bone structure of the nose, in which case the medical practitioner cannot have a direct view of the operative end of the surgical instrument.

Moreover, the techniques currently used in the field of rhinoplasty most frequently make use of conventional surgical instruments: osteotomes, gouges, bone chisels, either manually actuated using a mallet or combined with a small motor-type electrical actuator.

In the field of precision surgery the use of instruments excited by a mechanical movement at ultrasonic frequency is also known, such as for example those described in document WO2008012359.

Regarding the field of mandible and maxilla surgery, also referred to as "dentofacial osteotomy", this surgery is practiced through the patient's mouth, without any visible external scar, whether it concerns maxilla osteotomy (upper jaw) or mandible osteotomy (lower jaw). In particular, some mandible osteotomies require to cut some rear part of the mandible wherein the operative site cannot be seen directly by the practitioner, such a configuration being part of the techniques known as 'closed'.

The techniques known as 'closed' involve smaller scars or no scar at all, and more rapid patient recovery; thus, the inventors have revealed a need to improve the techniques of the prior art in the context of the operations known as 'closed', in which the surgeon does not have a direct view of the clinical site.

SUMMARY

To this end, a subject of the invention is an ultrasonic surgical instrument comprising a proximal portion forming a socket intended to be attached to an ultrasonic vibration generating device, and a distal portion, said instrument extending from the proximal portion to the distal portion along a main longitudinal axis, said instrument comprising a fluid channel, the distal portion comprising a cutting portion, at least a fluid port and at least one radial bump extending radially outwardly, said radial bump having a longitudinal position in correspondence with the longitudinal position of the cutting portion, whereby the radial bump provides a tactile mark (a location point) for the surgeon which can locate the distal portion, in particular the cutting portion, through the skin when said instrument is slid beneath the skin and when the surgeon cannot have a direct view of the distal portion. This locating function is particularly suitable for surgery of the rhinoplasty type in the technique known as 'closed'.

In various embodiments of the invention, use can furthermore optionally be made of one and/or another of the following provisions:

Preferably, there are provided two radial bumps, i.e. a first radial bump in correspondence with a first end of the cutting portion and a second radial bump in correspondence with the second end of the cutting portion; whereby the surgeon can have a tactile aid to locate the cutting segment in its entirety.

According to an option, the first radial bump and the first end of the cutting portion are situated at a same first axial position and the second radial bump and the second end of the cutting portion are situated at a same second axial position; whereby the surgeon can precisely locate the cutting segment in its entirety, the bumps and the ends of the cutting portion being arranged opposite each other in a radial direction perpendicular to the main longitudinal axis.

Said radial bump can be axially offset by a predetermined distance with regard to the cutting portion, with the distal portion exhibiting a bend whose end bears the cutting portion; thus the surgeon is provided with the ability to locate the cutting portion even in the case of a curved distal portion.

The instrument can advantageously comprise an intermediate portion with two consecutive bent portions having respective inclinations opposed and symmetrical with respect to the longitudinal axis; whereby this intermediate portion acts as an amplifier and/or impedance adaptor of the ultrasonic vibrations.

The first bent portion is inclined with an angle comprised between 5° and 20° with respect to the main longitudinal axis; which makes it possible to obtain an optimized amplification effect for the transmission of the ultrasonic vibrations.

The proximal portion extends along a first longitudinal axis X1 and the distal portion extends along a second longitudinal axis X2, either angularly offset with regard to the first axis, or parallel to the first axis but laterally offset with regard to the first axis; whereby the form of the instrument can have a shape particularly suitable for each surgical operation envisaged, in particular for rhinoplasty operations.

The cutting portion can be fitted with teeth 20; which forms an effective solution for osteotomy operations on bone or cartilage structure.

The cutting portion can extend parallel to the main longitudinal axis X; which proves practical in the case of incision along the bridge of the nose.

The cutting portion can extend transversally to the main longitudinal axis X; which proves practical in the case of transverse incision with respect to the bridge of the nose.

The cutting portion can extend along a direction inclined with regard to main axis X, with a predefined angle between 15° and 100°, preferably between 60° and 90°.

The distal portion is preferably fitted with at least two fluid outlet ports, one on each side of the cutting portion. This makes it possible to optimize the cooling of the clinical site and the cooling of the instrument.

The cutting portion can be formed as a grater. This makes it possible to locally flatten the bone surface.

The cutting portion can be formed as a part of a ball. This makes it possible to obtain a slightly concave bone and/or cartilage surface.

BRIEF DESCRIPTION OF THE DRAWINGS

The present invention will be better understood and other features and advantages will also become apparent on reading the following detailed description comprising embodiments given by way of example with reference to the attached figures, in which.

DETAILED DESCRIPTION

The same references in different figures denote identical or similar elements.

Figure 1:
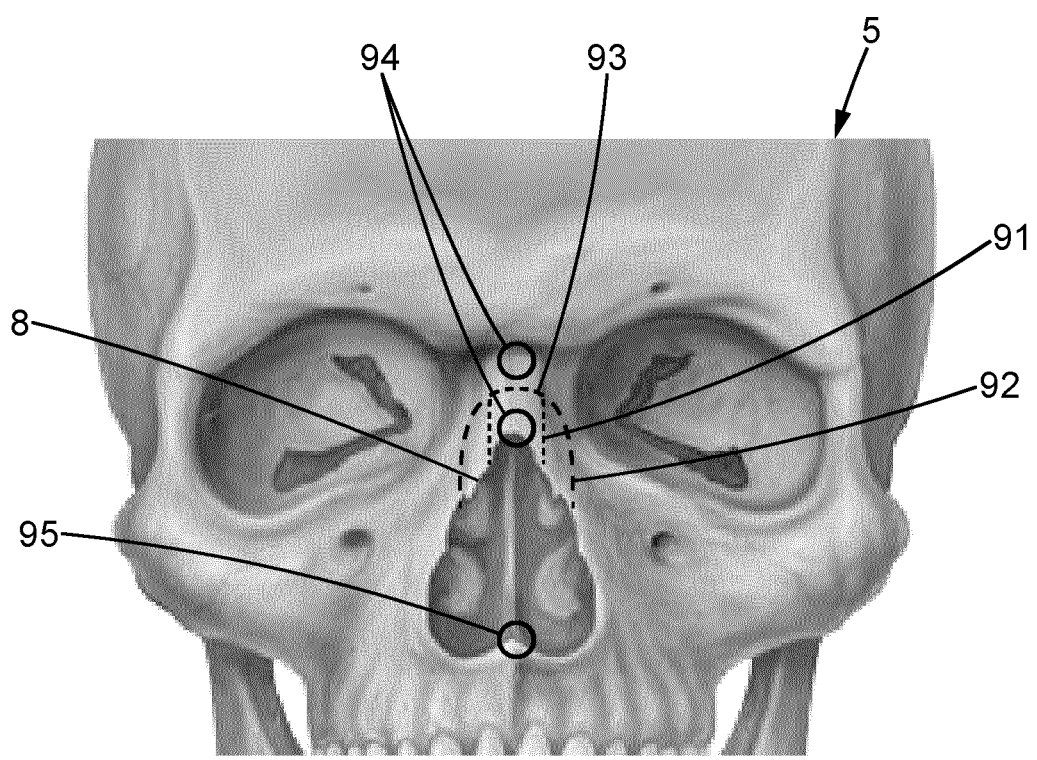
FIG. 1 is a general view of the bone structure around a person's nose.

FIG. 1 is a partial view of a cranium (or skull) 5 with the bone structure 8 of a person's nose. Apart from the bone structure, the nasal appendage also comprises a cartilage structure not shown in FIG. 1.

Surgical operations on the bone and cartilage structure of the nose can relate to different situations, among others: reparative surgery after trauma, correction of the position of the nasal septum and finally, more and more frequently, plastic surgery which consists of changing the aesthetic appearance of the patient's nose.

This involves in particular carrying out osteotomy operations to remove the bone tissues, in particular a medial osteotomy in the area referenced 91, a lateral osteotomy in the area referenced 92, a transverse osteotomy in the area referenced 93. The operation can also consist of remodelling the bone structure by abrasion, in particular in the areas referenced 94 and 95 (upper and lower base of the nose).

Figure 2:
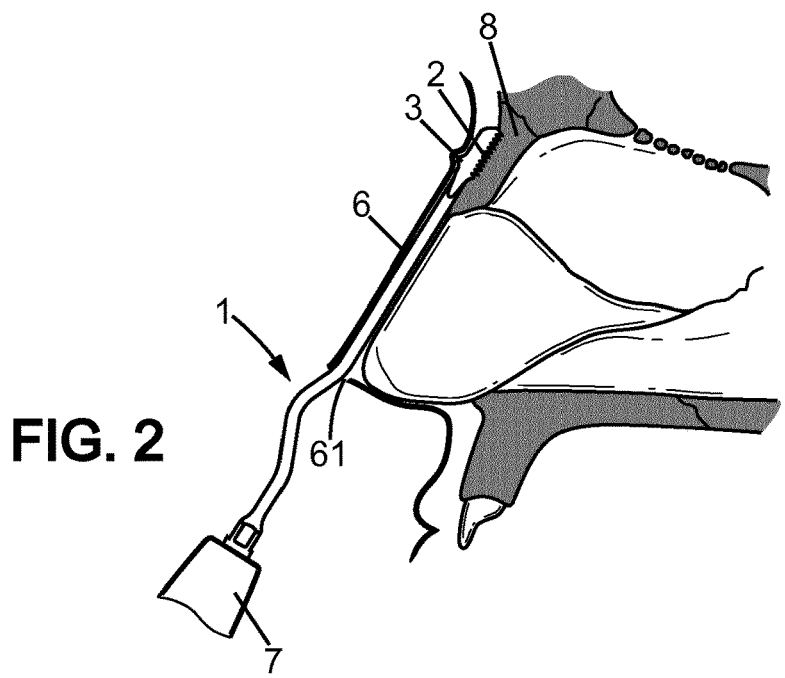
FIG. 2 is a profile view showing diagrammatically a medial osteotomy configuration with the surgical instrument according to the invention.

Within the context of the surgical operations known as 'closed', the operation areas 91-95 are reached by making an incision 61 of limited size in the base of the nostril. After this, as shown in FIG. 2, the surgeon will slide a surgical instrument 1 between the skin 6 on the one hand and the bone and cartilage structure of the nose on the other hand.

Within the context of the present invention, preferentially a surgical instrument of the ultrasonic type is used, i.e. to which an ultrasonic vibration generating device 7 imparts small-amplitude movements at frequencies in the ultrasonic band, making it possible to preserve the soft tissues (muscles, blood vessels, nerves) by working selectively only on the harder tissues (bone and cartilage).

In the closed technique, the surgeon does not have a direct view of the clinical operating site; advantageously according to the present invention, the surgical instrument is fitted with a tactile location means which can facilitate the surgeon's task.

Of course, it should be noted that the surgical instruments described in the present application can be used not only in the context of the technique known as 'closed', but also in the context of the technique known as 'open'.

More precisely, the surgical instrument 1 comprises in its distal portion a cutting portion 2, provided in order to abrade the bone or cartilage structure, and opposite this cutting portion, at least one radial bump 3 is provided.

By radial bump is meant a projection extending in a direction substantially perpendicular to the main longitudinal axis X of the surgical instrument, said axial direction being in particular most frequently coincident with the axis of the distal portion.

The radial bump exhibits a convex shape without a sharp edge, so as not to cause any wound on the inner surface of the skin 6, but nevertheless still clearly perceptible to touch by the practitioner. The height of the radial bump, with respect to the body of the instrument, is preferably selected between 0.5 mm and 1 mm. The apex of the bump is preferably rounded.

It should be noted that such bump, also called 'projection', is localized and allows accurate location of the cutting portion, it can be referred to as a 'point' bump.

The surgical instrument 1 is produced from stainless steel, for example a stainless steel for medical use, or another metal alloy for medical use.

Figure 3:
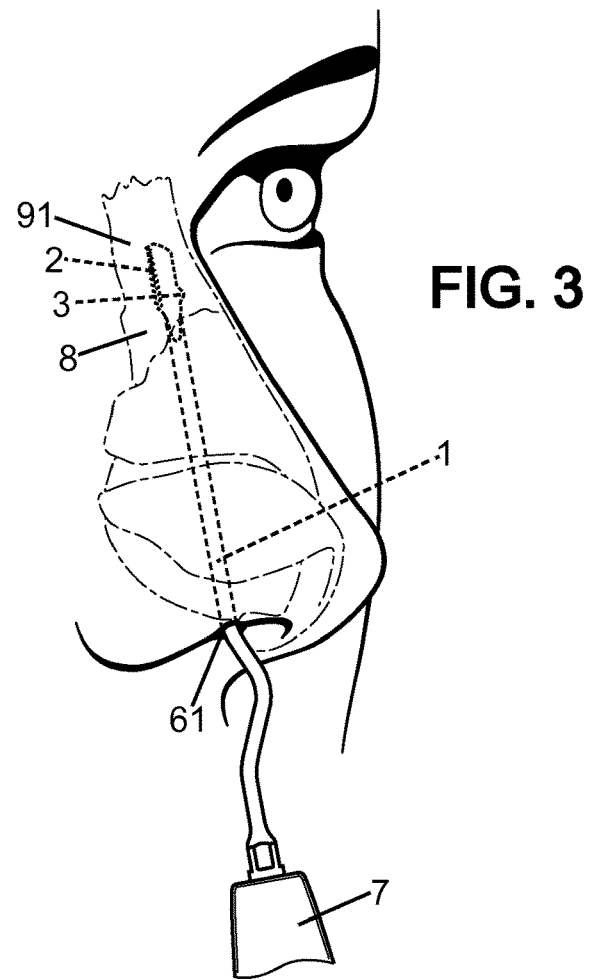
FIG. 3 is a three-quarter face view showing a lateral osteotomy configuration with the surgical instrument according to the invention.
Figure 4A:
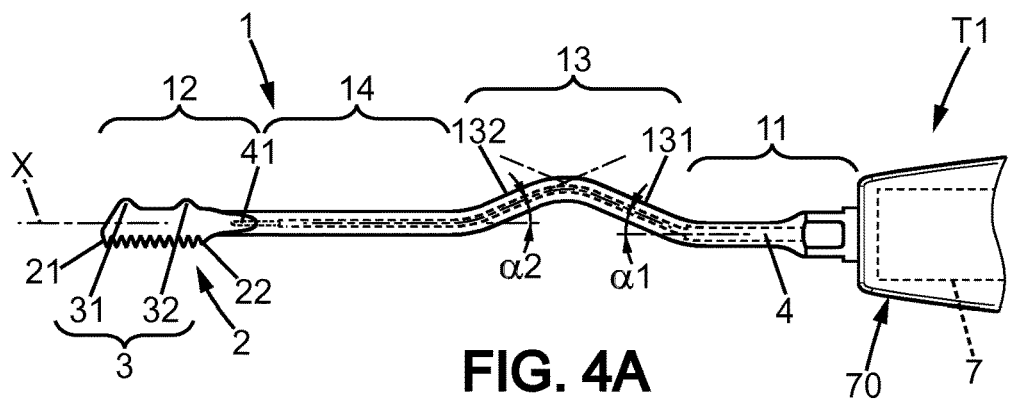
FIGS. 4A and 4B show a first type of instrument, a saw-type instrument for medial osteotomy, viewed from the side and from below respectively.
Figure 4B:
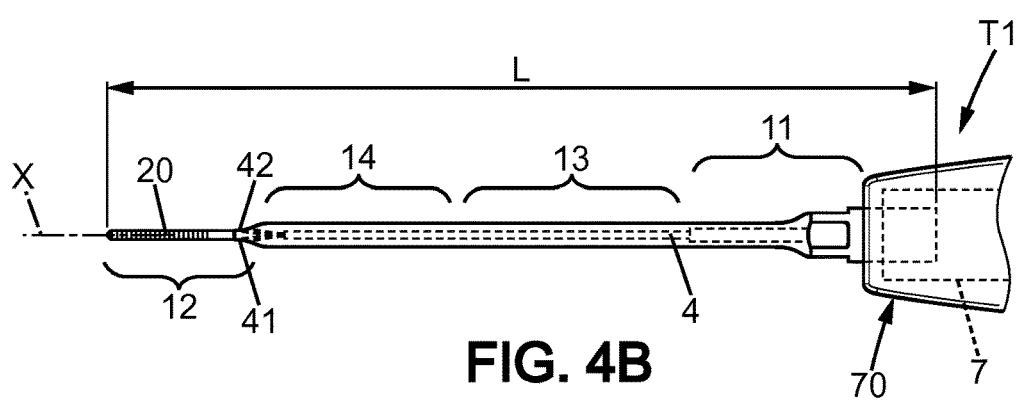
Figure 5A:
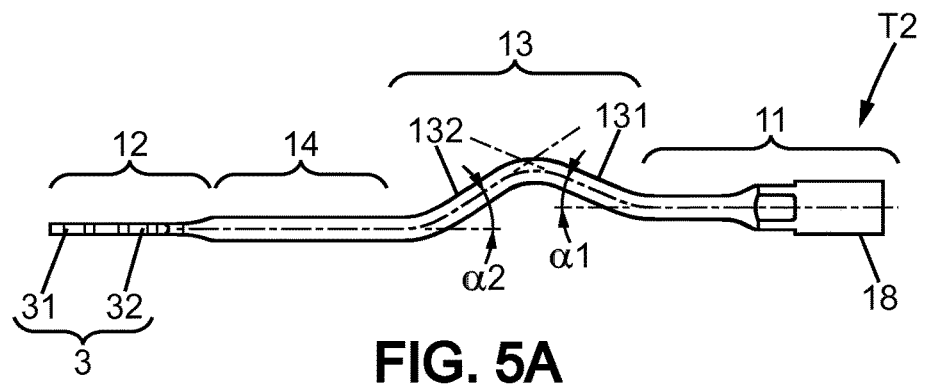
FIGS. 5A and 5B show a second type of instrument, a saw-type instrument for lateral osteotomy, viewed from the side and from above respectively.
Figure 5B:
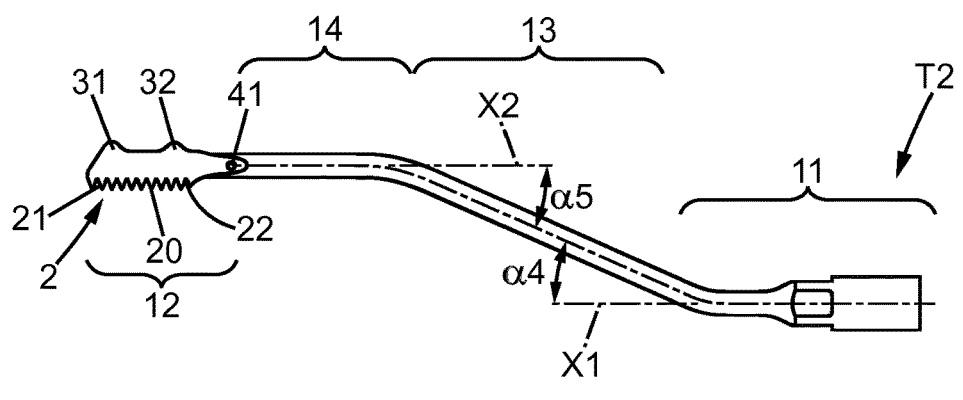
Figure 6A:
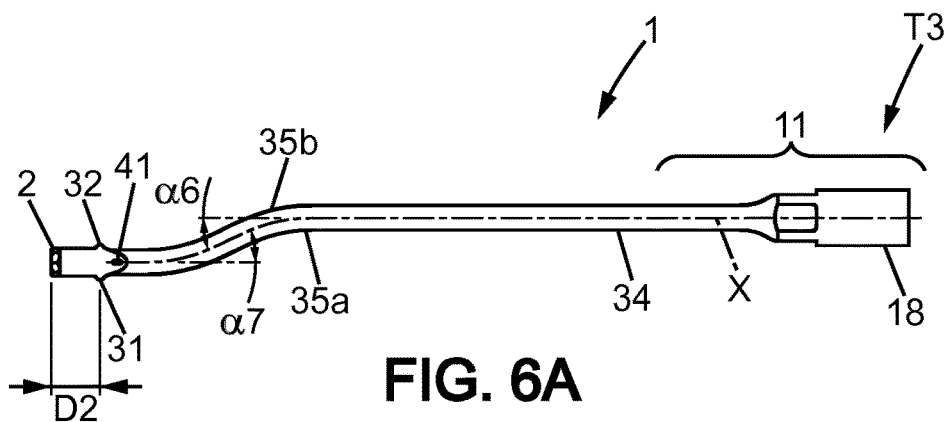
FIGS. 6A and 6B show a third type of instrument, a saw-type instrument for transverse osteotomy, viewed from the side and from above respectively.
Figure 6B:
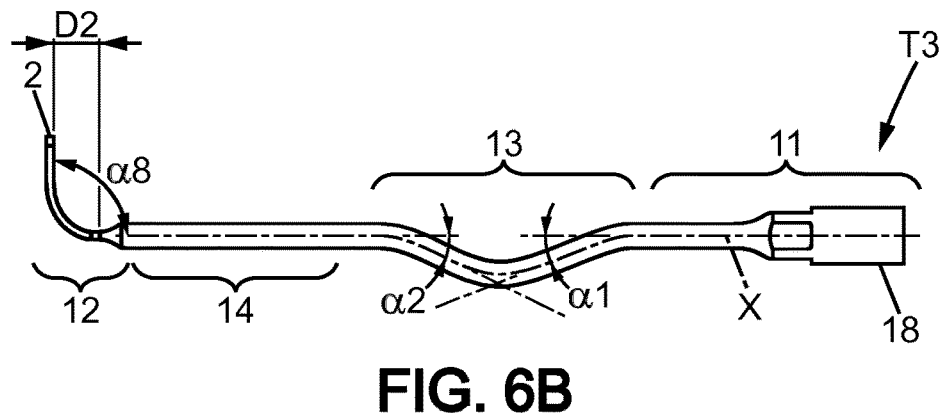
Figure 7A:
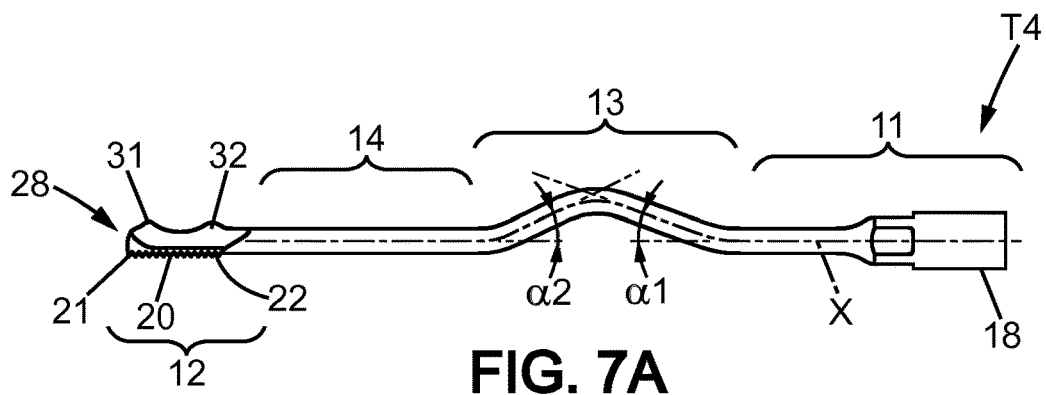
FIGS. 7A and 7B show a fourth type of instrument, a grater-type instrument, viewed from the side and from above respectively.
Figure 7B:
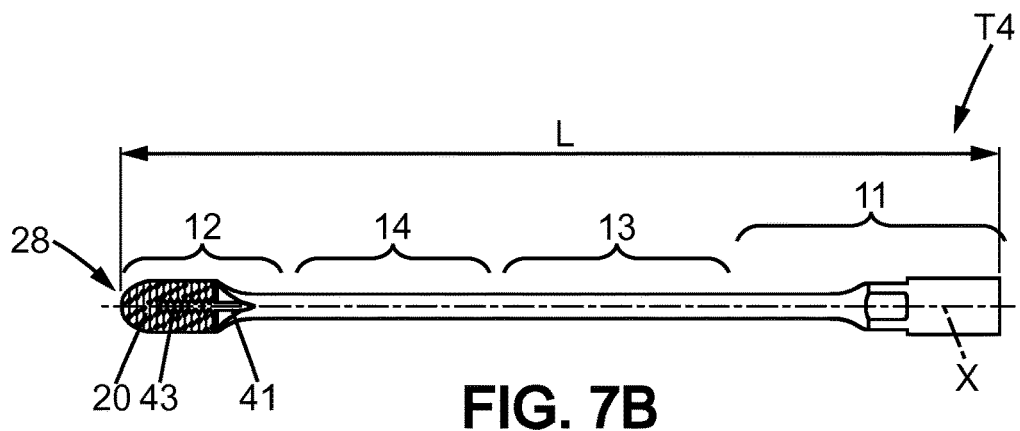
Figure 8A:
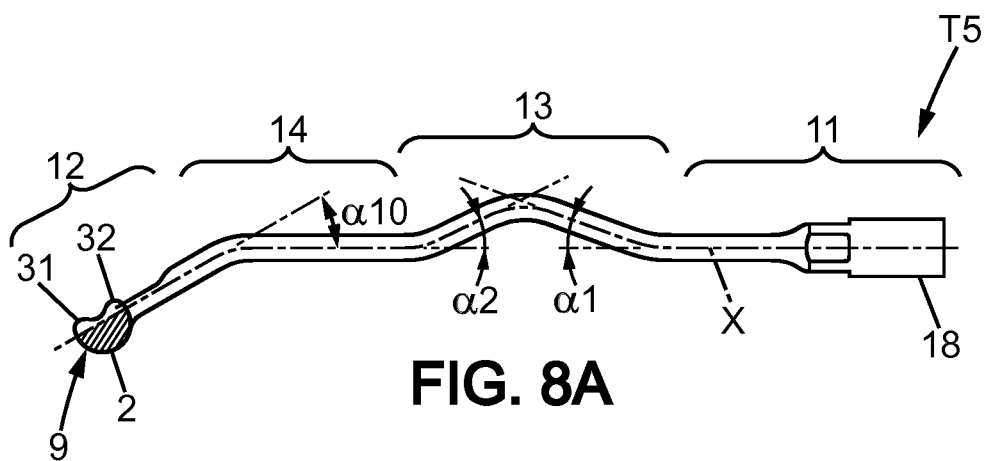
FIGS. 8A and 8B show a fifth type of instrument, an instrument of the diamond ball type, viewed from the side and from above respectively.
Figure 8B:
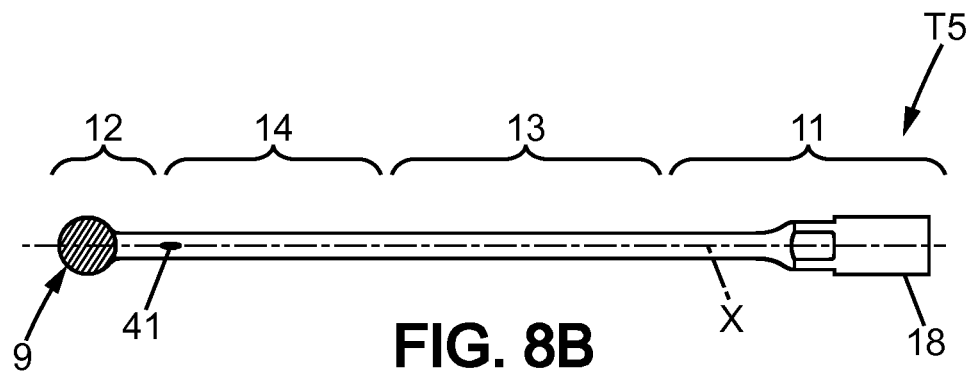

As shown in FIG. 3, according to the operating technique known as 'closed', in order to prepare for the operation, the surgeon makes an incision 61 at the base of the patient's right nostril, preferably in an inner area of the base of the nostril whereby the resulting scar will be almost invisible. Another incision is made symmetrically in the left nostril (not shown). Then the surgeon slides the surgical instrument 1 upwards until the cutting portion 2 reaches the target clinical site 91.

As shown in FIG. 2, the aforementioned radial bump forms a corresponding bump beneath the skin 6 which can be detected by touch by the surgical practitioner.

As shown in FIGS. 4 to 9, several variants T1,T2,T3,T4, T5 of surgical instruments 1 are presented. However all of them comprise the following common features:

a proximal portion 11 intended to be attached to the ultrasonic vibration generating device 7, which comprises a socket 18 attached by clipping, screwing or pinning to the vibration generating device, a distal portion 12, comprising the aforementioned cutting portion 2 and radial bump 3, a first intermediate portion 13 adjacent to the proximal portion, a second intermediate portion 14 interposed between the first intermediate portion and the distal portion 12.

The surgical instrument 1 extends from the proximal portion to the distal portion along a main longitudinal axis X.

The surgical instrument also comprises a fluid channel 4, which makes it possible to convey an irrigation and cooling fluid to the clinical site.

The first intermediate portion 13 can advantageously comprise two consecutive bent portions 131,132 having inclinations opposed and symmetrical with respect to the main longitudinal axis, in order to contribute to the efficient transmission of the ultrasonic vibrations from the generating device 7 to the distal portion 12, the detail of the geometry of these offset portions being given hereinafter.

Specifically, the range of ultrasonic frequencies preferably used in the intended applications extends from 26 kHz to 36 kHz, preferably in the range 30-33 kHz, and further preferably in 28-32 kHz.

According to a first particular variant T1 (FIGS. 4A, 4B), the surgical instrument 1 has a total length L comprised between 60 mm and 80 mm; the proximal portion 11 has a length comprised between 10 mm and 20 mm. The first intermediate portion 13, with the two bent portions 131,132 has a length comprised between 20 mm and 35 mm. The second intermediate portion 14 has a length comprised between 10 mm and 30 mm.

The main body of the surgical instrument 34 has a constant cross section, which allows relatively straightforward production, including for the formation of the irrigation channel 4.

The diameter of the fluid channel 4 is of the order of 0.5 mm in the example shown.

Over the majority of the length where the cross section is substantially constant, the diameter of the body 34 of the instrument is comprised between 1 mm and 3 mm.

The first bent portion 131 deviates from the axis X of the proximal portion by an angle $\alpha 1$, preferably comprised between 5° and 20°; similarly the second bent portion 132 deviates from the axis X of the distal portion by an angle $\alpha 2$, preferably also comprised between 5° and 20° and advantageously symmetrical with the angle $\alpha 1$.

Advantageously in this case, the first radial bump 31 has a position along the axis identical to the axial position of the front end 21 of the cutting portion. Similarly, the second radial bump 32 has a position along the axis identical to the axial position of the rear end 22 of the cutting portion. This makes it possible for the surgeon to locate the position of the cutting segment of the distal portion 12 very precisely.

According to a second particular variant T2 (FIGS. 5A, 5B), in addition to the features previously described in respect of the first variant, in the surgical instrument 1 the first and second intermediate portions 13,14 are laterally offset. A first bend having an angle $\alpha 4$ is arranged in the proximal portion or at the start of the first intermediate portion, a second bend having an angle $\alpha 5$ being arranged in the second intermediate portion.

Such an offset configuration makes it possible to reach and to work in the central area 94 of the nose, having introduced the surgical instrument 1 through one of the aforementioned lateral incisions 61. Such an offset configuration also makes it possible to work in lateral areas 92 of the bone structure of the nose.

According to a third particular variant T3 (FIGS. 6A, 6B), the surgical instrument 1 has a bent distal portion, in the example shown, with a 90° bend. It should be noted that the amplitude $\alpha 8$ can be comprised between 45° and 130°. Here, the cutting portion is located further away from the axis of the distal portion. In this particular case, the two radial bumps 31,32 have an axially offset position with regard to the axial position of the cutting portion, the offset being referenced by the predetermined length D2; for example the value of D2 being between 3 mm and 5 mm.

In this third variant, there is also shown an optional lateral offset arranged in the second intermediate portion 14; more precisely, this second intermediate portion 14 comprises a bend at locations 35a,35b having an angle $\alpha 6$ relative to the main axis and a further opposed bend having an angle $\alpha 7$.

According to a further option of this third variant, such lateral offset is not provided and the second intermediate portion 14 is aligned with the main axis X and the proximal portion.

As the bent distal portion is flat and has a minimal thickness, the two fluid outlet ports 41,42 are arranged close to the position of the radial bumps.

According to a fourth particular variant T4 (FIGS. 7A, 7B), instead of a distal portion in form of a saw, the surgical instrument 1 has a distal portion in the form of a grater 28. The operative portion of the grater is relatively flat, and comprises a central channel 43 for supplying the irrigation fluid, which complements a fluid port 41 at a point in the rear portion of the grater.

The radial bumps 31,32 are arranged on the main axis opposite the front end of the grater and the rear end of the grater respectively.

According to a fifth particular variant T5 (FIGS. 8A, 8B), instead of a distal portion in the form of a saw, the surgical instrument 1 has a distal portion in the form of a hemispherical grater 9, also called a part of a ball. Once again, the radial bumps 31,32 are arranged on the main axis opposite the front end of the grater forming a hemisphere and the rear end of the grater forming a hemisphere respectively. The second intermediate portion 14 comprises a bend having an angle $\alpha 10$ relative to the main axis X and a fluid outlet port 41.

Figure 9:
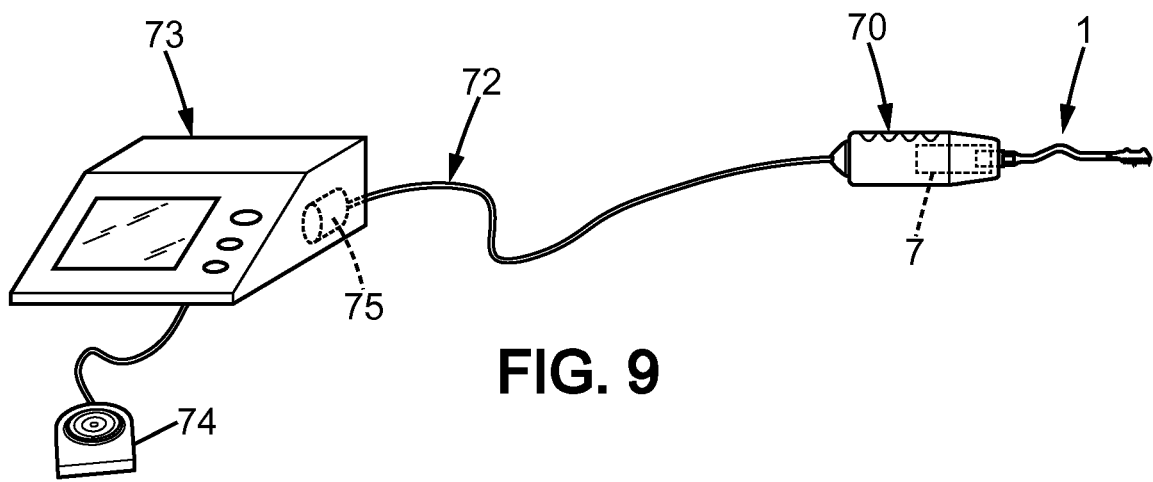
FIG. 9 is a diagrammatic view of a system in which the instrument is used.

As shown in FIG. 9, in a typical configuration, the surgical tool 1 is mounted on a handpiece 70 which contains the aforementioned ultrasonic generating device 7, said handpiece 70 being linked by a flexible tube 72 to a main appliance 73.

The flexible tube 72 contains electrical wires and a fluid channel. The main appliance 73 also contains a peristaltic pump 75 which impels the irrigation fluid toward the surgical instrument.

The surgeon uses a foot (pedal) control 74 to control the generation of ultrasonic vibrations as well as the activation of the peristaltic pump 75.

Advantageously according to the present invention, it is understood that despite not having a direct view of the clinical site, the surgeon is able to identify the position of the cutting portion of the instrument accurately by touching the radial bump in correspondence with the cutting portion in the distal portion.

The tactile referencing and accurate locating of the clinical site can advantageously be complemented by location marks on the patient's skin, made with coloured felt-tip pen by the surgeon before the start of the surgical operation itself. During the operation, the surgeon can thus align the radial bump with the mark(s) in coloured felt-tip on the skin, which proves to be particularly practical and greatly improves the precision of the surgical gesture.

Figure 10:
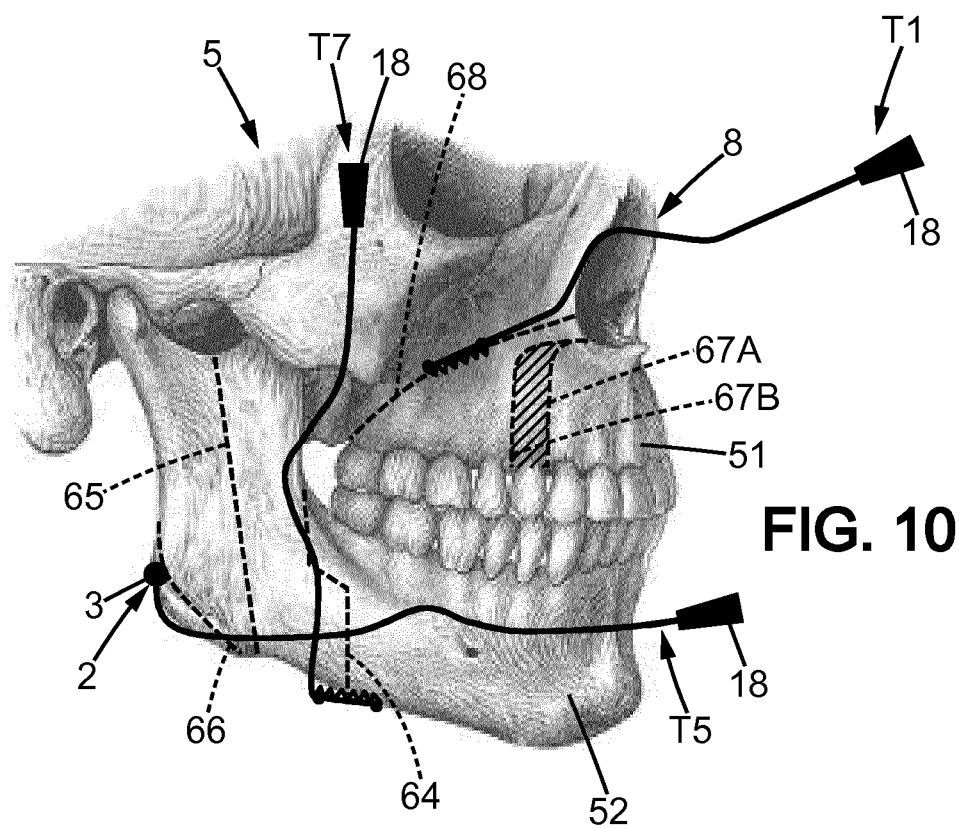
FIG. 10 illustrates schematically a mandible surgical operation with several different surgical instruments according to the invention.
Figure 11:
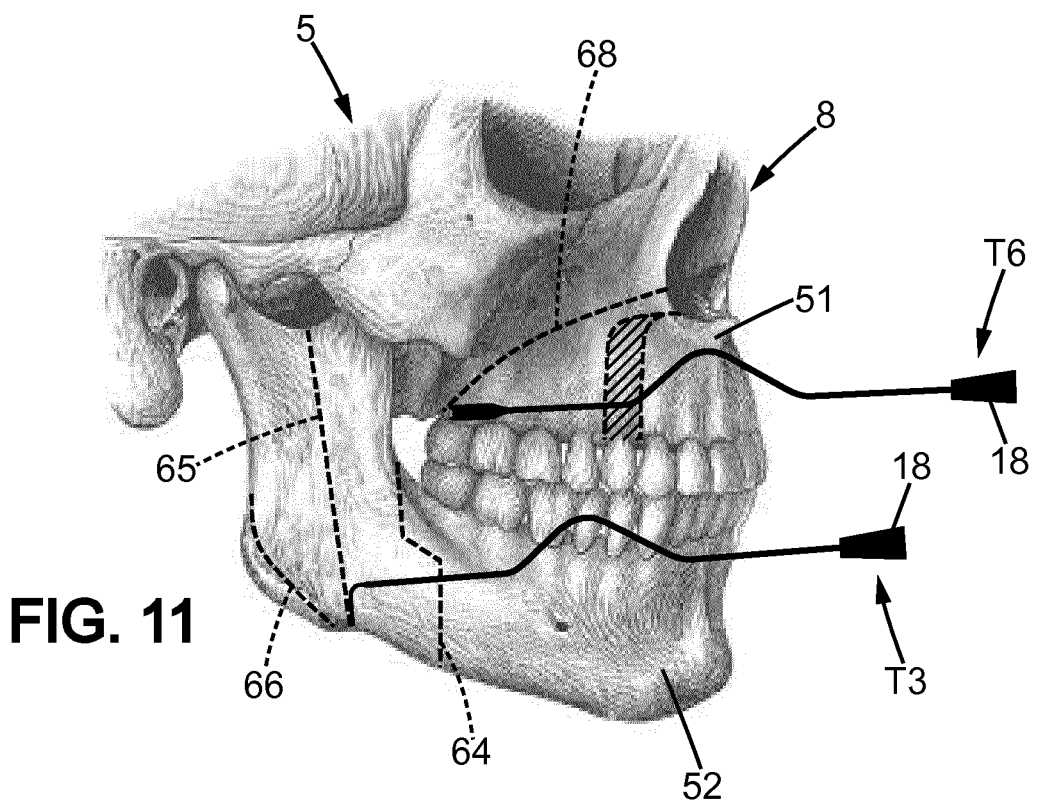
FIG. 11 illustrates schematically a maxilla surgical operation with several surgical instruments according to the invention.

Further, at FIGS. 10 and 11, there is shown a portion of a human skull 5 with a maxilla 51 and a mandible 52. Several possible osteotomies are also shown. A cut line referred to as 64 is the location of an osteotomy for a "Sagittal Split Ramus Osteotomy". This procedure is used to correct mandible retrusion and mandibular prognathism as known per se.

Another cut line referred to as 65 is another location of an osteotomy for a "IVRO: Intraoral Vertical Ramous Osteotomy".

Another cut line referred to as 66 is another location of an osteotomy for a "Angle Splitting Osteotomy". This procedure is used to round the angle of the low rear portion of the mandible, with the help of the fifth type T5 of surgical instrument.

Regarding now maxilla surgery, a further cut out part referred to as 67A, 67B is another location of an osteotomy for a "Segmental Osteotomy". The cut out part can be removed for palatal revision, and the maxilla 51 will be immobilized in a more backward position.

Another cut line referred to as 68 is another location of a maxilla osteotomy for a "Le Fort I Osteotomy". The cut out part can be moved for suitable position and immobilized at the position. In other words, the maxilla 51 can be moved to longitudinal direction, horizontal direction and vertical direction by this surgical procedure. And also these ultrasonic surgical instruments (shown in FIGS. 4A-8B, FIGS. 12-13) can be used for the "Le Fort II Osteotomy" or "Le Fort III Osteotomy".

For the above jaw surgical procedures, the surgeon can use one or more of the surgical instruments 1 already disclosed above, with a cutting portion 2 and at least a radial bump 3, preferably two radial bumps 31,32 corresponding to the ends 21,22 of the cutting portion 2.

This is practically useful when the surgeon cannot see directly the operative site and can just sense the tip of the instrument under the skin or tissue (subcutaneous configuration).

Various variants of the surgical instruments 1 already disclosed above (T1-T5) can also be used for the above jaw surgical procedures.

Figure 12:
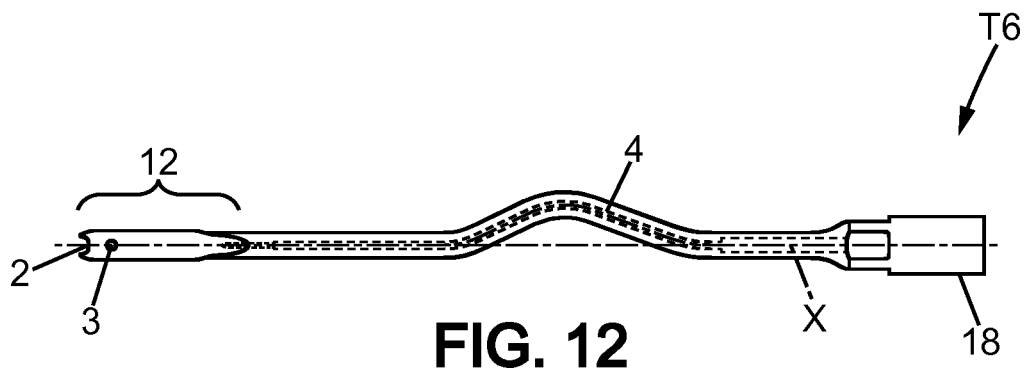
FIG. 12 shows a sixth type of surgical instrument.

Further, FIG. 12 shows a sixth type T6 of surgical instrument, with a cutting portion 2 disposed transversally at the tip of the distal portion, likewise forming a small size scalpel.

Figure 13:
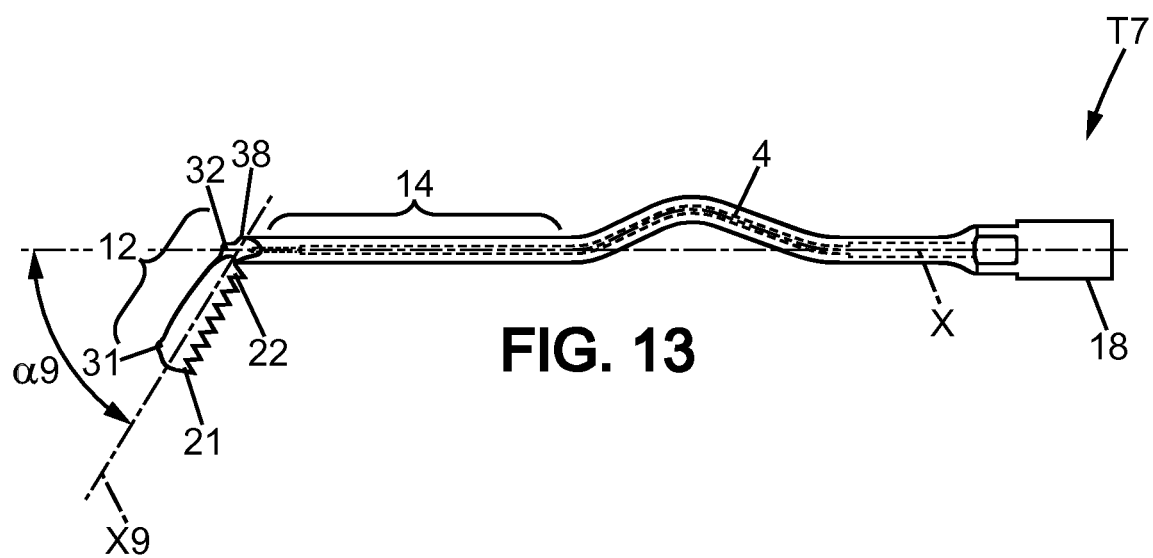
FIG. 13 shows a seventh type of surgical instrument.

Further, FIG. 13 shows a seventh type T7 of surgical instrument, with a distal portion 12 extending along a direction X9, which is inclined with regard to main axis X with a predefined angle α9 comprised between 15° and 100°, preferably between 60° and 90°. More precisely, at the end of the second intermediate portion 14 (aligned with X), there is a short bent section 38, and the distal portion 12 extends therefrom along a direction X9, with a cutting portion 2 on one side away from the main axis and two bumps 31,32 on the back side thereof. The cutting portion 2 (here likewise a blade) may be straight or slightly concave.

As shown on FIG. 10, for a "Sagittal Split Ramus Osteotomy" (cut line referred to as 64), the seventh type T7 of surgical instrument can be used to cut the underside portion of the mandible, the surgeon can sense the radial bumps under the skin.

For a "IVRO: Intraoral Vertical Ramous Osteotomy" (cut line referred to as 65), the third type T3 of surgical instrument can be used to cut the side mandible bone.

As shown on FIG. 11, for a "Le Fort I Osteotomy", (cut line referred to as 68), the first type T1 of surgical instrument can be used to cut the medium and front parts of the maxilla bone, and the sixth type T6 of surgical instrument can be used to cut the rear part of the maxilla bone.

Regarding the various possible types of surgical instruments, there can be provided geometric variations of the first intermediate portion 13 and the second intermediate portion 14, as per their respective length, bend portions, so the surgeon can reach easily the operative site on the mandible and maxilla.

The invention claimed is:

1. An ultrasonic surgical instrument having a proximal portion having a first longitudinal axis and forming a socket intended to be attached to an ultrasonic vibration generating device, and a distal portion having a second longitudinal axis, the instrument extending from the proximal portion to the distal portion, said instrument comprising a fluid channel,
   wherein the distal portion comprises a cutting portion, at least a first fluid port, and wherein there is provided a first radial bump and a second radial bump, the first radial bump located on a first end of the distal portion and the second radial bump is located on a second end of the distal portion, wherein the second longitudinal axis extends from the first end of the distal portion to the second end of the distal portion,
   wherein the first and second radial bumps are disposed on a first side of the distal portion relative to the second longitudinal axis and the cutting portion is disposed on a second side of the distal portion opposite the first side relative to the second longitudinal axis,
   whereby the surgeon can have a tactile aid to locate in its entirety a cutting segment extending from a first end of the cutting portion to a second end of the cutting portion.

2. The instrument according to claim 1, wherein the first radial bump and the first end of the cutting portion have a same first axial position and the second radial bump and the second end of the cutting portion have a same second axial position; whereby the surgeon can precisely locate the cutting segment in its entirety.

3. The instrument according to claim 1, wherein the instrument comprises an intermediate portion with two consecutive bent portions having inclinations opposed and symmetrical with respect to the first longitudinal axis, whereby the intermediate portion acts as an ultrasonic vibrations amplifier.

4. The instrument according to claim 1, wherein the distal portion extends either angularly offset with regard to the first longitudinal axis, or parallel to the first longitudinal axis but laterally offset with regard to the first longitudinal axis.

5. The instrument according to claim 1, wherein the cutting portion is fitted with teeth.

6. The instrument according claim 1, wherein the cutting portion extends parallel to the first longitudinal axis.

7. The instrument according to claim 1, wherein the cutting portion extends perpendicularly to the first longitudinal axis.

8. The instrument according to claim 1, wherein the cutting portion extends along a direction inclined with regard to the first longitudinal axis, with a predefined angle between 15° and 100°.

9. The instrument according to claim 1, wherein the distal portion is fitted with at least a second fluid port, wherein the first and second fluid ports are arranged one on each side of the cutting portion.

10. The instrument according to claim 1, wherein the cutting portion is formed as a grater.

11. The instrument according to claim 1, wherein the cutting portion is formed as a part of a ball.

* * * * *